(12) United States Patent
Gollapudy et al.

(10) Patent No.: US 7,414,153 B2
(45) Date of Patent: Aug. 19, 2008

(54) PROCESS FOR PREPARATION OF OPTICALLY ACTIVE 1-ERYTHRO-2-AMINO-1-PHENYL-1-PROPANOL

(75) Inventors: Subrahmanyam Gollapudy, Hyderabad (IN); Sunil Vaman Joshi, Mahad (IN)

(73) Assignee: Emmellen Biotech Pharmaceuticals Limited, Mumbai (IN)

( * ) Notice: Subject to any disclaimer, the term of this patent is extended or adjusted under 35 U.S.C. 154(b) by 152 days.

(21) Appl. No.: 11/578,362

(22) PCT Filed: Mar. 9, 2005

(86) PCT No.: PCT/IN2005/000075

§ 371 (c)(1),
(2), (4) Date: Oct. 13, 2006

(87) PCT Pub. No.: WO2005/100299

PCT Pub. Date: Oct. 27, 2005

(65) Prior Publication Data

US 2007/0203363 A1 Aug. 30, 2007

(30) Foreign Application Priority Data

Apr. 15, 2004 (IN) .................. 448/MUM/2004

(51) Int. Cl.
*C07B 57/00* (2006.01)
*C07C 209/00* (2006.01)
(52) U.S. Cl. ...................... 564/304; 564/357
(58) Field of Classification Search ............ None
See application file for complete search history.

(56) References Cited

FOREIGN PATENT DOCUMENTS

| DE | 587586 | 10/1933 |
|---|---|---|
| DE | 588880 | 11/1933 |
| DE | 599433 | 6/1934 |
| DE | 639126 | 11/1936 |
| DE | 1014553 | 8/1957 |
| DE | 2258410 | 6/1974 |
| DE | 2558507 | 9/1976 |
| DE | 2854070 | 6/1979 |
| EP | 1 142 864 | 10/2001 |
| GB | 365535 | 1/1932 |
| GB | 365541 | 1/1932 |
| GB | 1385409 | 2/1975 |
| IN | 172970 | 9/1989 |
| JP | 05 004948 | 1/1993 |

OTHER PUBLICATIONS

Adkins et al. "The Preparation of Raney Nickel Catalysts and their Use Under Conditions Comparable with Those for Platinum and Palladium Catalysts" *Contribution from the Laboratory of Organic Chemistry*, University of Wisconsin vol. 70 pp. 695-698 (1948).

Hartung et al. "Amnio Alcohols. I. Phenylpropanolamine and Para-Tolylpropanolamine" *Contribution from the Research Labortories of Sharp and Dohme*. vol. 51 pp. 2262-2266 (1929).

Kreutz et al. "Bakers yeast reduction of (E)-1-phenyl-1,2-propanedion 2-(O-methyloxime). A key step for a (−)-norephedrine synthesis" *Tetrahedron: Asymmetry* vol. 8 pp. 2649-2653 (1997).

Koga et al. "Studies on Optically Active Amnio Acids, Stereoselective Synthesis of *l*-Norephedrine Hydrochloride from D-Phenylalanine" *Chem. Pharm. Bull* vol. 14. No. 3 pp. 243-246 (1966).

Jackson et al. "Applications of Optically Active Aryl Cyanohydrins in the Synthesis of α-Hydroxy Aldehydes, α-Hydroxy Ketones and β-Hydroxy Amines" *Aust. J. Chem* vol. 43 pp. 2045-2062 (1990).

Hoover et al. "Synthesis of 2-Amnio-1-Phenyl-1-Propanol and its Methylated Derivatives" *Contribution from the Department of Chemistry and Purdue Research Foundation*, Purdue University vol. 12 pp 506-509 (1947).

Science and Culture. vol. 23, No. 6. pp. 313-314 ; Dec. 1957.

J. Am. Chem. Soc. vol. 114, No. 14 pp. 5900-5902 (1992).

Matsumoto et al. "Synthesis of 1-Phenylpropane Derivatives" Contribution from the Chemistry Department of Faculty of Science, Hokkaido University vol. 79 pp. 5506-5508 (1957).

Osterreichische Chemiker-Zeitung. Kurze wissenschaftliche Mitteilungen- Versammlungs-und Vortragsberichte vol. 57 pp. 308-309 (1956).

Evdokimoff. "Riduzioni con lega Ni-Al. Applicazioni alla sintesi della norefedrina e di altre ammine farmacologicamente attive" *Gazz. Chim. Ital.* vol. 81 pp. 725-734 (1951).

Subramanian et al. "Synthesis of (1RS, 2SR)-(±)-2-Amnio-1-phenyl-1-propanol from (R)-(−)-1- Hydroxy-1-phenyl-2-propanone" *J. Chem.Tech. Biotechnol.* vol. 39 pp. 215-218 (1987).

Jarowski et al. "Amnio Alcohols. XII. Optical Isomers In The Ephedrine Series of Compounds (1)" *Contribution of the Research Laboratories*, School of Pharmacy, University of Maryland vol. 8 pp. 564-571 (1943).

Hey, "NOR-*dl*-Ephedrine and NOR-dl-ψ-Ephedrine" J. Chem. Soc. pp. 1232-1324 (1930).

Nagai et al. "Ober die Synthese der isomeren Ephedrine und ihrer Homologen" *Ann. Chem.* vol. 470 pp. 157-182 (1929).

Müller, Partielle asymmetrische Synthesen von Ephedrinkörpern unter dem Einfluβ von Seitenketten-und Kernsubstituenten. I. Mitt. *Annalen(Justus Liebigs Annalen Der Chemie)* vol. 598 pp. 70-84 (1956).

Hartung, "Palladium Catalysis. IV. Change in the Behavior of Palladium-on-Charcoal in Hydrogenation Reactions" *Contribution from the School of Pharmacy*, University of North Carolina pp. 5927-5929 (1952).

*Primary Examiner*—Samuel A Barts
(74) *Attorney, Agent, or Firm*—Hamre, Schumann, Mueller & Larson, P.C.

(57) ABSTRACT

An efficient cost-effective process for preparation of 1-erythro-2-amino-1-phenyl-1-propanol from 1-1-phenyl-1-hydroxy-2-propanone, which comprises converting 1-1-phenyl-1-hydroxy-2-propanone to 1-1-phenyl-1-hydroxy-2-propanone oxime and reducing the oxime with a catalyst consisting of finely divided nickel and aluminium metals giving good diastereomeric purity and yield.

15 Claims, No Drawings

PROCESS FOR PREPARATION OF OPTICALLY ACTIVE 1-ERYTHRO-2-AMINO-1-PHENYL-1-PROPANOL

TECHNICAL FIELD

The present invention relates to an efficient process for preparation of 1-erythro-2-amino-1-phenyl-1-propanol from 1-1-phenyl-1-hydroxy-2-propanone.

The present invention particularly relates to an efficient process for preparation of optically active 1-erythro-2-amino-1-phenyl-1-propanol (1-Norephedrine), free from its optical antipode and free from diastereomeric impurities.

BACKGROUND OF THE INVENTION 1-erythro-2-Amino-1-phenyl-1-propanol, 1, is a naturally occurring alkaloid found in the Chinese herb 'Ma Huang'. It is isolated from the herb along with 1-ephedrine and other alkaloids.

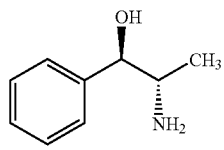

Apart from the natural source, this material has been produced synthetically also. The synthetic methods can be broadly classified into following categories:

1. Resolution of dl-phenylpropanolamine, which in turn is prepared by:

i) catalytic hydrogenation of alpha-isonitrosopropiophenone (scheme 1)

Scheme 1

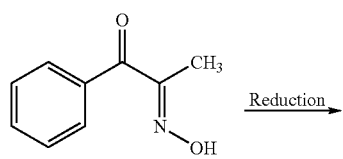

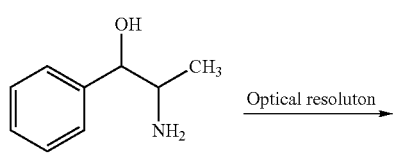

l-erythro-2-amino-1-phenyl-1-propanol ii) alpha halogenation of propiophenone, amination followed by catalytic hydrogenation. (scheme 2, X=halogen)

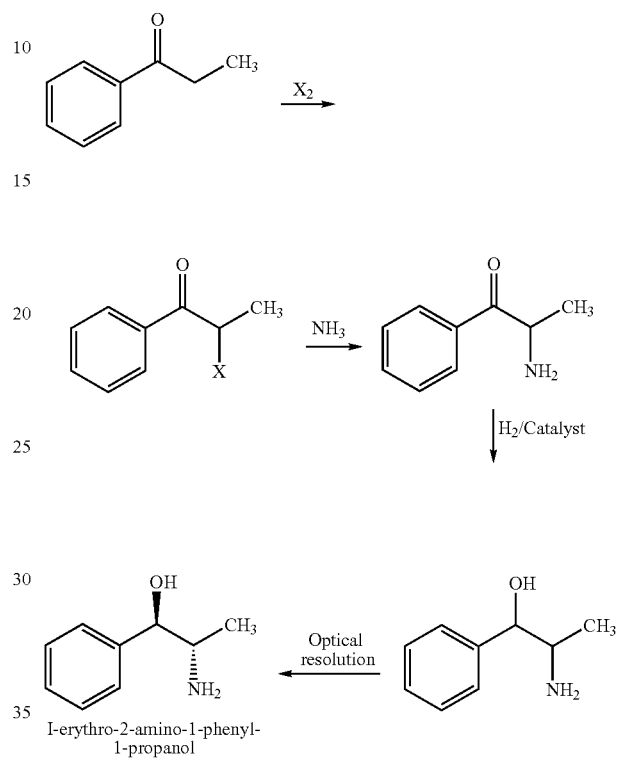

iii) Reduction of 1-phenyl-2-nitro-1-propanol (scheme 3)

Scheme 3

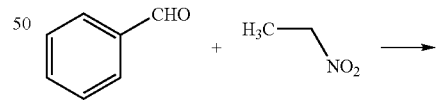

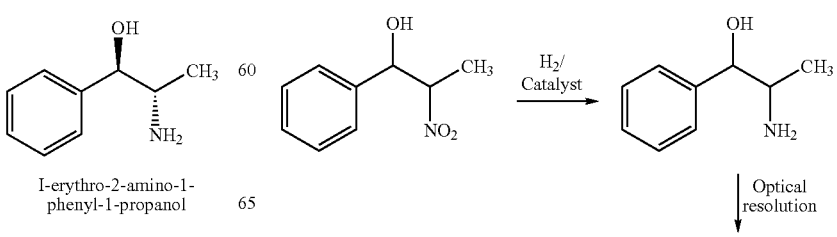

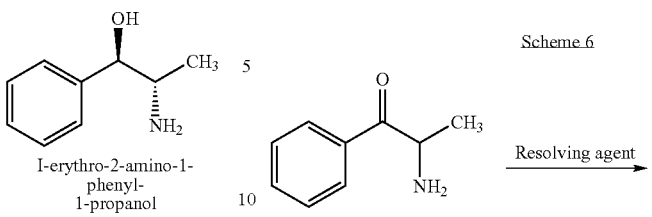

I-erythro-2-amino-1-phenyl-1-propanol

2. Catalytic hydrogenation of 1-1-phenyl-1-hydroxy-2-propanone in the presence of ammonia or aralkylamines. (Scheme 4, R=H, aralkyl)

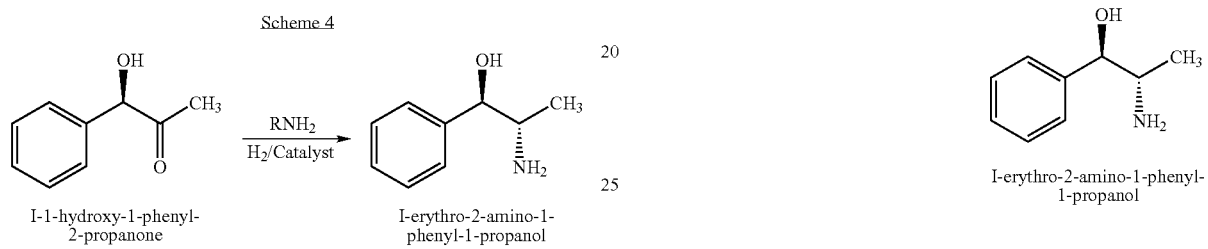

Scheme 4

I-1-hydroxy-1-phenyl-2-propanone → I-erythro-2-amino-1-phenyl-1-propanol

3. Reduction of derivatives like oximes, hydrazones or imines of 1-1-phenyl-1-hydroxy-2-propanone by catalytic hydrogenation, which may be effected by chiral or achiral catalysts or by dissolving metals or metal amalgams. (Scheme 5, R=OH, $NH_2$, aralkyl)

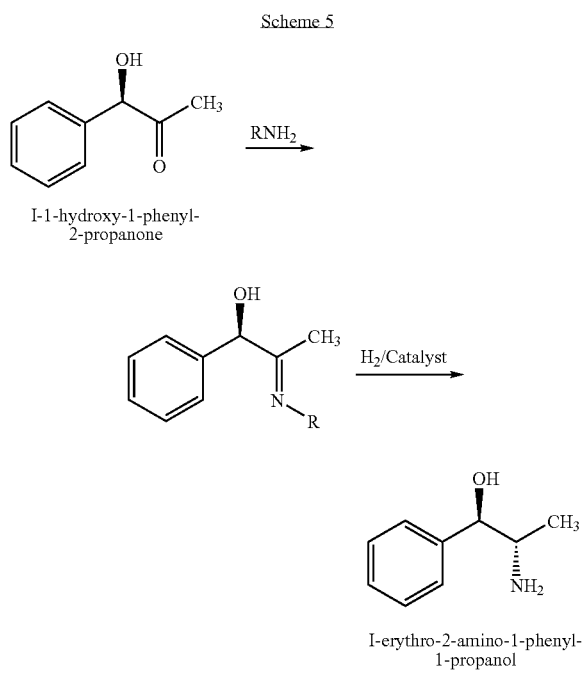

Scheme 5

I-1-hydroxy-1-phenyl-2-propanone

I-erythro-2-amino-1-phenyl-1-propanol

4. Resolution of 2-amino-1-phenyl-1-propanone followed by catalytic hydrogenation of optical antipode of 2-amino-1-phenyl-1-propanone (Scheme 6)

Scheme 6

I-erythro-2-amino-1-phenyl-1-propanol

5. Stereospecific synthesis using chiral precursors with known stereochemistry or chiral auxiliaries.

The resolution of dl-phenylpropanolamine has been tried by employing many resolving agents S. Kanao, J. Pharm. Soc. Japan 48, 947-958 (1928); E. Flassig, Oesterreich Chemiker Zeitung 57, 308 (1956); and J. Org. Chem. 25, 1929-1937 (1960) disclose use of L-tartaric acid as a resolving agent.

C. Jarowsky; W. H. Hartung, J. Org. Chem. 8, 654 (1943) disclose use of L-mandelic acid as a resolving agent.

H. Takamatsu, J. Pharm. Soc. Japan 76, 1230-1233 (1956) disclose use of camphorsulphonic acid as a resolving agent.

Several patent documents also disclose methods for resolving dl-phenylpropanolamine using various resolving agents. Some of these patents are incorporated below for reference.

German Patents 2,258,410 (1973); 2,304,055 (1974) and 2,258,410 (1974) and British Patent 1,385,490 (1975) disclose resolution of dl-phenylpropanolamine employing thiazolidinecarboxylic acids.

German Patent 2,258,507 (1976) discloses resolution of dl-phenylpropanolamine using pantoic acid.

German patents 2,854,069 (1979) and 2,854,070 (1979) demonstrate use of maleamides of d- and l-norpseudoephedrine in resolving dl-phenylpropanolamine.

Japanese Patent 4530 (1955) discloses resolution of dl-phenylpropanolamine using (2R,3R)-2,3-dimethoxy succinic acid.

However, none of these resolving agents used in prior art give good yields of optically pure antipodes of phenylpropanolamine. Besides, the cost and difficulty in recovery of these resolving agents is of great concern.

In addition, the starting material dl-phenylpropanolamine itself has been prepared by a number of methods U.S. Pat. No. 3,028,429 (1962); W. H. Hartung; J. C. Munch, J. Am. Chem. Soc. 51, 2262-2266 (1929); U.S. Pat. No. 2,784,228 (1957); W. H. Hartung, Y. Chang, J. Am. Chem. Soc. 74, 5927-5929 (1952); H. Adkins, H. R. Billica, J. Am. Chem. Soc. 70, 695-698 (1948); M. C. Rebstock; G. W. Moersch; A. C. Moore and J. M. Vandenbelt, J. Am. Chem.

Soc. 73, 3666-3670 (1951) and T. Matsumoto; K. Hata, J. Am. Chem. Soc. 79, 5506 (1957) describe in details the preparation of dl-phenylpropanolamine by catalytic hydrogenation of alpha-isonitrosopropiophenone with metal catalysts such as Ni, Pd, Pt etc.

J. R. Merchant, R. K. Pandya, J. N. Ray, Science and Culture, Calcutta 23, 313-314 (1957) describe the preparation of dl-phenylpropanolamine by reduction of alpha-isonitrosopropiophenone with aluminum amalgam.

D. H. Hey, J. Chem. Soc. 1232 (1930) demonstrate the preparation of dl-phenylpropanolamine by reduction of alpha-isonitrosopropiophenone with sodium/ethanol V. Evdokimoff, Gazz. Chim. Ital. 81, 725 (1951) describe the preparation of dl-phenylpropanolamine by reduction of alpha-isonitrosopropiophenone with nickel-aluminium (1:1) alloy.

Other methods of preparation of dl-phenylpropanolamine as described in German Patent 468,306 (1925); H. K. Mueller, Annallen 598, 70-84 (1956) and P. Besse, H. Veschambre, J. Org. Chem. 59, 8288-8291 (1994) include reduction of 2-aminopropiophenone, which in turn is obtained by a) halogenation of propiophenone and reaction with ammonia, b) reaction of halogenated propiophenone with sodium azide followed by reduction of alpha-azidopropiophenone.

Racemic phenylpropanolamine is also obtained by reduction of 1-phenyl-2-nitro-1-propanol as discussed in literatures like N. Wilhelm; Nagai; S. Kanao, Annallen 470, 157-182 (1929); S. Kanao, J. Pharm. Soc. Japan 48, 947-958 (1928); Y. Shirozaki, J. Pharm. Soc. Japan 51, 720-722 (1931); F. W. Hoover, H. B. Hass, J. Org. Chem. 12, 506 (1947) as well as disclosed in patent documents U.S. Pat. No. 2,151,517 (1939) and British Patent 1,413,930 (1975).

These methods however have potential problems regarding poor efficiencies of conversion, contamination with diastereomeric impurities, which necessitate laborious purifications and catalyst cost.

Other methods as disclosed in German Patents 588,880 (1933); 587,586 (1933); 599,433 (1934); British Patents 365, 535 (1930); 365,541 (1930); Indian Patent IN172,970 (1994) as well as exemplified in P. M. Subramanian; S. K. Chatterjee and M. C. Bhatia, J. Chem. Tech. Biotechnol. 39, 219-229 (1987) involving reductive amination of 1-1-phenyl-1-hydroxy-2-propanone are also riddled with problems.

The starting material, 1-1-phenyl-1-hydroxy-2-propanone, being an alpha-ketol, is very sensitive to extreme pH and temperature conditions. It is known to undergo very rapid racemization and isomerization to 2-hydroxy-1-phenyl-1-propanone in presence of traces of alkalies or acids (G. Richard, Compt. Rend. 214, 673 (1942)). Due to this the processes described in these references cause extensive racemization of 1-1-phenyl-1-hydroxy-2-propanone and subsequently lower the yields of 1-erythro-2-amino-1-phenyl-1-propanol.

In fact, low to medium yields of racemic phenylpropanolamine have been reported by this method in Indian Patent IN 172,970 (1994); P. M. Subramanian; S. K. Chatterjee and M. C. Bhatia, J. Chem. Tech. Biotechnol. 39, 219-229 (1987) in spite of starting with optically active 1-1-phenyl-1-hydroxy-2-propanone.

British Patent 365,535 (1930); German patent 1,014,553 (1957) and O. C. Kreutz; P. J. S. Moran and J. A. R. Rodrigues, Tetrahedron: Asymmetry 8, 2649-2653 (1997) have disclosed reduction of derivatives like oxime, hydrazone, N-benzylimine etc. of 1-1-phenyl-1-hydroxy-2-propanone. The oximes, oxime ethers and hydrazones of 1-phenyl-1-hydroxy-2-propanone have been reduced by catalytic hydrogenation and by aluminum amalgams.

European Patent EP 1,142,864 (2003) discloses reduction of N-benzylimine by catalytic hydrogenation.

Similarly, the approaches based on resolution of 2-amino-1-phenyl-1-propanone followed by reduction are not free from problems.

These approaches are disclosed in German patent 639,129 (1936); Japanese Patent JP 63091352 (1988) and literatures like H. Takamatsu, J. Pharm. Soc. Japan 76, 1219-1222 (1956) and B. D. Berrang, A. H. Lewin, F. I. Carroll, J. Org. Chem. 47, 2643-2647 (1982).

The starting material 2-amino-1-phenyl-1-propanone is stable only in salt form and unstable as a base and known to undergo self condensation to give undesired by-products which include 2,5-dimethyl-3,6-diphenyl-2,5-dihydropyrazine (M. Tiffeneau; J. Levy and E. Ditz, Bull Soc. Chim. 2, 1848 (1935) and S. Gabriel, Chem. Ber. 41, 1127-1156 (1908)). The resolution efficiency is poor and overall yield of the optically pure antipodes of erythro-2-amino-1-phenyl-1-propanol is also very low.

The catalytic hydrogenation of 2-amino-1-phenyl-1-propanone as described in F. Skita, F. Keil, E. Baesler, Chem. Ber. 66, 858 (1932), does not give exclusively erythro-product which is very essential for overall efficiency of the process.

One more method has been described in Jpn. Kokai Tokkyo Koho JP 0504948 [93,04948] (1993) in which alpha-isonitrosopropiophenone is asymmetrically hydrogenated in the presence of chiral substituted ferrocene catalysts. However this method also does not give a high diastereomeric and enantiomeric excess of one enantiomer of phenylpropanolamine over other and hence was not satisfactory.

Another approach is a stereospecific synthesis of 1-erythro-2-amino-1-phenyl-1-propanol from chiral precursors (T. F. Buckley; H. Rapoport, J. Am. Chem. Soc. 103, 6157-6163 (1981); K. Koga; H. Matsou and S. Yamada, Chem. Pharm. Bull. 14, 243-246 (1966); W. R. Jackson; H. A. Jacobs; G. S. Jayatilake; B. M. Matthews and K. C. Watson Aust. J. Chem. 43, 2045 (1990)) or by use of chiral auxiliaries. (W. Oppolzer; O. Tamura; G. Surendrababu and M. Signer, J. Am. Chem. Soc. 114, 5900 (1992))

In addition to the above, methods have been described by D. Enders; H. Lotter; N. Maigrot; J. P. Mazaleyrat and Z. Welvart, Nouv. J. Chem. 8, 747-750 (1984), and in Jpn. Kokai Tokkyo Koho JP 10 45688 (1998) in which alpha-isonitrosopropiophenone was either hydrogenated in the presence of hydrogenations having chiral ligands or reduced with borohydride complexes of 1,2-amino alcohol chiral auxiliaries.

A review of prior art methods shows that all the above stated methods suffer from at least one of the following drawbacks: cost and recyclability of hydrogenation catalyst, cost and recyclability of resolving agents, poor diastereo- and enantioselectivity in reductions, cost and availability of chiral precursors or chiral auxiliaries, cost and availability of chiral catalysts.

Thus there is a long felt consistent need to develop a process for the preparation of 1-erythro-2-amino-1-phenyl-1-propanol (1-Norephedrine) that bypasses the above limitations and is more efficient in terms of yield and resolution and at the same time is cost-effective.

These considerations have thus motivated the present inventors to address the existing need of a better and cost effective method for preparation of 1-erythro-2-amino-1-phenyl-1-propanol (1-Norephedrine).

OBJECTS OF THE INVENTION

It is thus an object of the invention to provide a process for the preparation of 1-erythro-2-amino-1-phenyl-1-propanol that overcomes the drawbacks existing with the prior art. It is a further object of the invention to provide a process for preparation of optically active 1-erythro-2-amino-1-phenyl-1-propanol (1-Norephedrine), free from its optical antipode.

It is a further object of the invention to provide a process for preparation of optically active 1-erythro-2-amino-1-phenyl-1-propanol (1-Norephedrine) free from diastereomeric impurities (norpseudoephedrine).

Yet another object of the invention is to provide a process for the preparation of 1-erythro-2-amino-1-phenyl-1-propanol that has not only good resolution efficiency but also a high overall yield of the optically active 1-erythro-2-amino-1-phenyl-1-propanol. A further object of the invention is to provide a process for the preparation of 1-erythro-2-amino-1-phenyl-1-propanol that is cost effective and simple.

Yet another object of the invention is to provide a process for the preparation of 1-erythro-2-amino-1-phenyl-1-propanol that is economically attractive and industrially feasible.

Yet another object of the invention is to provide a process for the preparation of 1-erythro-2-amino-1-phenyl-1-propanol that avoids use of complex and cost extensive resolving agents, chiral precursors or chiral auxiliaries or chiral catalysts.

SUMMARY OF THE INVENTION

Thus according to an aspect of the present invention there is provided a process for preparation of 1-erythro-2-amino-1-phenyl-1-propanol from 1-1-phenyl-1-hydroxy-2-propanone comprising steps of:
  i) reacting 1-1-phenyl-1-hydroxy-2-propanone with an oximation agent in the presence of a base to form 1-1-phenyl-1-hydroxy-2-propanone oxime
  ii) reducing 1-1-phenyl-1-hydroxy-2-propanone oxime using nickel aluminium catalyst mixture as reducing agent to obtain crude optically active 1-erythro-2-amino-1-phenyl-1-propanol base.

The oximation agent is preferably any hydroxylamine salt used in the presence of a base.

In accordance to a preferred aspect of the present invention, there is provided a process for preparation of 1-erythro-2-amino-1-phenyl-1-propanol from 1-1-phenyl-1-hydroxy-2-propanone comprising steps of:
  i) reacting 1-1-phenyl-1-hydroxy-2-propanone with a hydroxylamine salt in the presence of a base to form 1-1-phenyl-1-hydroxy-2-propanone oxime.
  ii) reducing 1-1-phenyl-1-hydroxy-2-propanone oxime using nickel aluminium catalyst mixture as reducing agent.
  iii) treating the crude product so obtained to get the pure isomer of 2-amino-1-phenyl-1-propanol.

DETAILED DESCRIPTION

The present invention thus provides an efficient process for preparation of optically active 1-erythro-2-amino-1-phenyl-1-propanol (1-Norephedrine), free from its optical antipode and free from diastereomeric impurities.

After considerable investigation of the prior art and various modifications thereof, it was concluded that all the methods involving use of 1-1-phenyl-1-hydroxy-2-propanone caused extensive racemization of the molecule. So, a new approach was required for development of cost effective process for preparation of 1-erythro-2-amino-1-phenyl-1-propanol from 1-1-phenyl-1-hydroxy-2-propanone.

The obvious choice of starting material was 1-1-phenyl-1-hydroxy-2-propanone since it has the right stereochemistry at C-1 carbon atom of the molecule. This compound is easily prepared by fermentative transformation of benzaldehyde. (P. I. Rogers; H. S. Shin; B. Wang, Adv. Biochem. Engg. 56, 33-59 (1997))

An important feature of the present invention is the reduction of 1-1-phenyl-1-hydroxy-2-propanone oxime by means of a reducing agent comprising of finely divided nickel and aluminium metals in a ratio from 1.5 to 5.0.

The oximation agent is preferably any hydroxylamine salt used in the presence of a base.

The preferred process according to the present invention is shown in the reaction Scheme depicted in reaction Scheme 7.

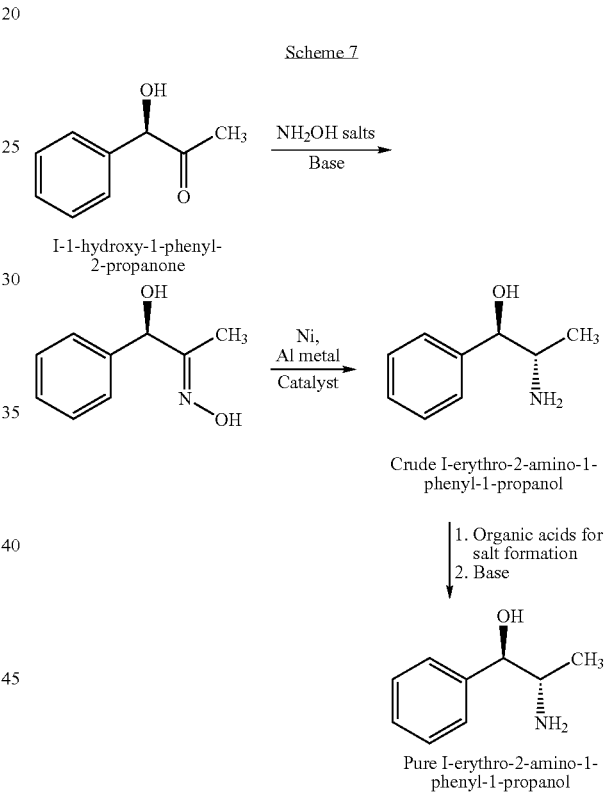

The preferred salts of hydroxylamine are hydrochloride, hydrobromide, sulphate and orthophosphate.

The base used for reaction is any suitable base or alternatively is selected from a group comprising of sodium carbonate, sodium hydrogen carbonate, sodium hydroxide, sodium acetate, potassium carbonate, potassium hydroxide, potassium acetate, calcium hydroxide, barium hydroxide, preferably, sodium hydroxide or sodium hydrogen carbonate.

The molar ratio of oximation agent, preferably hydroxylamine salt, to 1-1-phenyl-1-hydroxy-2-propanone is between 0.7 and 2.5, more preferably, between 1.0 and 1.50. The molar ratio of hydroxylamine salt to the base is adjusted such that the acidic counterpart of the hydroxylamine is completely neutralized.

The preferred temperature of reaction is between $-5°$ C. and $70°$ C., preferably between $0°$ C. and $30°$.

The reaction is carried out by mixing a solution of 1-1-phenyl-1-hydroxy-2-propanone in an organic solvent and a solution of hydroxylamine salt and the base in water.

The organic solvent for this purpose is any suitable solvent or alternatively is selected from diethyl ether, di-n-butyl ether, methyl-t-butyl ether, benzene, toluene, tetrahydrofuran, ethyl acetate or 1,2-dimethoxyethane.

The oxime of 1-1-phenyl-1-hydroxy-2-propanone so formed by the reaction between 1-1-phenyl-1-hydroxy-2-propanone and hydroxylamine salt in presence of base, is further isolated by conventional solvent extraction techniques involving separation of organic phase, extracting aqueous phase by the same organic solvent that was used for dissolving 1-1-phenyl-1-hydroxy-2-propanone, drying the organic phase over anhydrous sodium sulphate and evaporation in vacuo.

1-1-phenyl-1-hydroxy-2-propanone oxime so obtained is further reduced by reacting the 1-1-phenyl-1-hydroxy-2-propanone oxime with nickel aluminium catalyst mixture. The ratio of aluminium to nickel in the catalyst mixture is ranging from 1.5 to 5.0.

For this purpose, the 1-1-phenyl-1-hydroxy-2-propanone oxime is mixed with a solution of base in water. The base for this purpose is any conventional base preferably sodium hydroxide or potassium hydroxide. The molar ratio of base to 1-1-phenyl-1-hydroxy-2-propanone oxime is preferably between 1.0 and 5.0. The mixture of 1-1-phenyl-1-hydroxy-2-propanone oxime with base in water is treated with nickel aluminium catalyst mixture, the catalyst mixture is at least 0.4 to 1.0-times the weight of starting material i.e., 1-1-phenyl-1-hydroxy-2-propanone oxime preferably at least 0.6 to 1.0 times the weight of starting material.

The ratio of aluminium and nickel metals in the catalyst mixture is critical to getting the desired diastereomeric purity as well as to the yield of the product 1-erythro-2-amino-1-phenyl-1-propanol. With the ratio of aluminium to nickel below 1.5 or above 5.0, the yield and quality of the product 1-erythro-2-amino-1-phenyl-1-propanol is unsatisfactory.

Similarly, the ratio of the catalyst mixture to the starting material is a critical to getting higher yield of the product 1-erythro-2-amino-1-phenyl-1-propanol. The optimum range of the weight of the catalyst mixture is at least 0.4 to 1.0 times of the weight of the starting oxime. Quantities of the catalyst mixture below 0.4 times the weight of starting oxime are ineffective as there is no appreciable formation of product 1-erythro-2-amino-1-phenyl-1-propanol. With quantities above 1.0 times the weight of starting oxime, very violently exothermic runaway reaction sets in. Thus, the quantities above this ratio are not practically usable.

The temperature of reaction mixture before addition of nickel aluminium catalyst mixture is maintained preferably between −20° C. and +10° C. The temperature of reaction mixture is allowed to increase with a free exotherm up to 60° to 100° C., which leads to the formation of 1-erythro-2-amino-1-phenyl-1-propanol. 1-erythro-2-amino-1-phenyl-1-propanol, so formed, is further isolated by removal of catalyst sludge and extraction with organic solvent. The organic solvent is any suitable solvent or can be selected from toluene, benzene, 1,2-dichloroethane, di-n-butyl ether or diethyl ether. The product is recovered by solvent evaporation.

This crude product consists chiefly of 1-erythro-2-amino-1-phenyl-1-propanol, together with some of the diastereomer impurity, 1-threo-2-amino-1-phenyl-1-propanol.

Pure 1-erythro-2-amino-1-phenyl-1-propanol is obtained from this crude product by treatment with an organic acid in aqueous media or a lower aliphatic alcohol or a mixture of water and one of these alcohols or a mixture of two of these alcohols at a temperature between 0° and boiling point of the solvent at atmospheric pressure. The less soluble salt is filtered off. The desired isomer of 2-amino-1-phenyl-1-propanol, which forms less soluble salt The salt containing the desired isomer of 2-amino-1-phenyl-1-propanol is decomposed by treatment with a base and the base form of the desired isomer of 2-amino-1-phenyl-1-propanol is extracted using an organic solvent. Pure 1-erythro-2-amino-1-phenyl-1-propanol base is further isolated by evaporation of the solvent in vacuo.

The pure 1-erythro-2-amino-1-phenyl-1-propanol base thus isolated may be converted to salts with inorganic acids by treatment with appropriate inorganic acids.

The organic acid used for the separation of the erythro and threo isomers is preferably selected from a group comprising of acetic acid, propionic acid, butyric acid, isobutyric acid, oxalic acid, malonic acid, succinic acid, cyclohexane carboxylic acid, benzoic acid, p-toluic acid, methanesulphonic acid, p-toluenesulphonic acid.

The solvent used for this separation reaction is either water or a lower aliphatic alcohol preferably selected from a group comprising of methanol, ethanol, isopropyl alcohol, n-butanol, 2-butanol and tert-butanol or a mixture of water and one of these alcohols or a mixture of two of these alcohols.

The base used for decomposition of the organic acid salt of 1-erythro-2-amino-1-phenyl-1-propanol is preferably selected from a group comprising of sodium carbonate, sodium hydrogen carbonate, sodium hydroxide, sodium acetate, potassium carbonate, potassium hydroxide, potassium acetate, calcium hydroxide, barium hydroxide, preferably, sodium hydroxide or sodium hydrogen carbonate.

The solvent used for extraction of pure 1-erythro-2-amino-1-phenyl-1-propanol base is preferably selected from a group comprising of toluene, benzene, 1,2-dichloroethane, di-n-butyl ether or diethyl ether. The details of the invention, its objects and advantages are explained hereunder in greater detail in relation to non-limiting exemplary illustrations. The examples are merely illustrative and do not limit the teaching of this invention and it would be obvious that various modifications or changes in the procedural steps by those skilled in the art without departing from the scope of the invention and shall be consequently encompassed within the ambit and spirit of this approach and scope thereof.

The following method of analysis was followed for determination of diasteraomeric purity in the examples:

Diasteraomeric purity was ascertained using HPLC analysis carried out following the conditions given below:
1. Column: Discovery C-18 (Waters) 150 3.9 mm; 5 µm
2. Mobile phase:

20 ml of tetramethylammonium hydroxide (10% aq. Solution) and 5 ml of ortho phosphoric acid in distilled water, diluted to 1 liter and mixed well. To 956 ml of the above buffer, 40 ml methanol, 4 ml tetrahydrofuran is added, mixed well, filtered and degassed.

3. Detector, UV detector, wavelength 210 nm.
4. Flow rate: 1 ml/min.
5. Run time: 20 min.
6. Injection volume: 20 µl
7. Resolution solution: A solution in mobile phase containing 0.1 mg/ml of each of the 1-erythro-2-amino-1-phenyl-1-propanol HCl and 1-threo-2-amino-1-phenyl-1-propanol HCl reference standards. Resolution between the peaks due to 1-erythro-2-amino-1-phenyl-1-propanol HCl and 1-threo-2-amino-1-phenyl-1-propanol HCl should not be less than 2.0
8. Sample solution: 0.5 mg/ml in mobile phase Inject the sample solution in six replicate injections. The relative standard deviation on area of the peak corresponding to 1-norephedrine should not be more than 2.0. Calculate the content of 1-threo-2-amino-1-phenyl-1-propanol in the sample by area normalization method and express it as area %.

EXAMPLE 1

Example 1A

Preparation of 1-1-phenyl-1-hydroxy-2-propanone oxime 1-1-phenyl-1-hydroxy-2-propanone oxime can be prepared by any one of the non-limiting methods illustrated below i) To a solution of 1-1-phenyl-1-hydroxy-2-propanone (50 g) in 150 ml di-n-butyl ether is added a solution of 44 g of sodium acetate trihydrate ($CH_3COONa.3H_2O$) in 150 ml of water. The solution is chilled to 15° C. and a solution of 23 g hydroxylamine hydrochloride in 100 ml water is added. The whole mixture is vigorously agitated for 2 hours. Di-n-butyl ether layer is separated and evaporated in vacuo to yield 60 g of 1-1-phenyl-1-hydroxy-2-propanone oxime.

ii) 30 g of hydroxylamine hydrochloride is dissolved in 150 ml of water. The solution is chilled to 15° C. A solution of 18 g of sodium hydroxide in 150 ml water is added slowly to adjust pH to between 7.0 and 8.0. The mixture is chilled to −10° to −5° C. and a solution of 50 g of 1-1-phenyl-1-hydroxy-2-propanone in 150 ml of toluene is added and the whole mixture is stirred for 1 hour at the same temperature. The toluene layer is separated, dried over sodium sulphate and evaporated in vacuo to yield 60 g of 1-1-phenyl-1-hydroxy-2-propanone oxime.

Example 1B

Preparation of 1-erythro-2-amino-1-phenyl-1-propanol hydrochloride from 1-1-phenyl-1-hydroxy-2-propanone oxime 25 g of sodium hydroxide is dissolved in 350 ml of water. 50 g of 1-1-phenyl-1-hydroxy-2-propanone oxime is added to it. The solution is chilled to −15° C. 30 g of the nickel aluminium catalyst mixture (containing 60 parts by weight of aluminium and 40 parts by weight of nickel) is added to it. The mixture is vigorously stirred at −15° C. and then the temperature is allowed to rise as a free exotherm sets in. When the temperature reaches 75°, the exothermic tendency of reaction mixture subsides. 200 ml of 1,2-dichloroethane is added to the mixture and the catalyst sludge is filtered. 1,2-Dichloroethane is separated from the filtrate and aqueous layer is extracted again with 100 ml of 1,2-dichloroethane. The combined organic layer is washed with 100 ml water, dried over sodium sulphate and solvent removed in vacuo.

This gives 50 g of 1-erythro-2-amino-1-phenyl-1-propanol base. This is dissolved in absolute ether and treated with ethanolic hydrogen chloride to give 1-erythro-2-amino-1-phenyl-1-propanol hydrochloric acid.

mp 171-172°, alpha$_D$: −32.5° (5% in water)

Diastereomeric purity (HPLC): 1-erythro-2-amino-1-phenyl-1-propanol: 97.5%, 1-thero-2-amino-1-phenyl-1-propanol: 2.5%

EXAMPLE-2

Preparation of pure 1-erythro-2-amino-1-phenyl-1-propanol hydrochloride 25 g of crude 1-erythro-2-amino-1-phenyl-1-propanol base is dissolved in 100 ml of a 1:1 mixture of absolute ethanol and n-butanol. The mixture is heated to 60-65°. 20 g of benzoic acid is added to the mixture and the heating at 60-65° is continued for 2 hours. The mixture is cooled to 10° and the precipitate of 1-erythro-2-amino-1-phenyl-1-propanol benzoate salt is filtered. This salt is suspended in 100 ml water and treated with 10 g of sodium hydroxide and the liberated pure 1-erythro-2-amino-1-phenyl-1-propanol base is extracted with diethyl ether. Pure 1-erythro-2-amino-1-phenyl-1-propanol base is recovered by evaporation of the solvent in vacuo.

This yields 23 g of pure 1-erythro-2-amino-1-phenyl-1-propanol base. This may be further converted to hydrochloride by treatment with ethanolic hydrochloride to give pure 1-erythro-2-amino-1-phenyl-1-propanol hydrochloride.

mp: 173°, alpha$_D$: −33.8° (5% in water).

Diastereomeric purity (HPLC): 1-erythro-2-amino-1-phenyl-1-propanol: 99.8%, 1-thero-2-amino-1-phenyl-1-propanol: 0.2%

EXAMPLE 3

Preparation of 1-erythro-2-amino-1-phenyl-1-propanol hydrochloride using ratios of aluminium-nickel catalyst below 1.5 and above 5.0

Example 3A

With an Aluminium-nickel Catalyst in a Ratio of 55:45 (1.22)

25 g of sodium hydroxide is dissolved in 350 ml of water. 50 g of 1-1-phenyl-1-hydroxy-2-propanone oxime is added to it. The solution is chilled to −15° C. 30 g of the nickel aluminium catalyst mixture (containing 55 parts by weight of aluminium and 45 parts by weight of nickel) is added to it. The mixture is vigorously stirred at −15° C. and then the temperature is allowed to rise. An exotherm sets in and temperature increases up to 35° C. 200 ml of 1,2-dichloroethane is added to the mixture and the catalyst sludge is filtered. 1,2-Dichloroethane is separated from the filtrate and aqueous layer is extracted again with 100 ml of 1,2-dichloroethane. The combined organic layer is washed with 100 ml water, dried over sodium sulphate and solvent removed in vacuo. This gives 29 g of 1-erythro-2-amino-1-phenyl-1-propanol base.

This is dissolved in absolute ether and treated with ethanolic hydrogen chloride to give 1-erythro-2-amino-1-phenyl-1-propanol hydrochloric acid.

mp 163-165°, alpha$_D$: −26.5° (5% in water)

Diastereomeric purity (HPLC): 1-erythro-2-amino-1-phenyl-1-propanol: 83.9%, 1-thero-2-amino-1-phenyl-1-propanol: 16.2%

Example 3B

With an Aluminium-nickel Catalyst in a Ratio of 85:15 (5.67)

25 g of sodium hydroxide is dissolved in 350 ml of water. 50 g of 1-1-phenyl-1-hydroxy-2-propanone oxime is added to it. The solution is chilled to −15° C. 30 g of the nickel aluminium catalyst mixture (containing 85 parts by weight of aluminium and 15 parts by weight of nickel) is added to it. The mixture is vigorously stirred at −15° C. and then the temperature is allowed to rise. An exotherm sets in and temperature increases up to 95° C. 200 ml of 1,2-dichloroethane is added to the mixture and the catalyst sludge is filtered. 1,2-Dichloroethane is separated from the filtrate and aqueous layer is extracted again with 100 ml of 1,2-dichloroethane. The combined organic layer is washed with 100 ml water, dried over sodium sulphate and solvent removed in vacuo. This gives 22.5 g of 1-erythro-2-amino-1-phenyl-1-propanol base. This is dissolved in absolute ether and treated with ethanolic hydrogen chloride to give 1-erythro-2-amino-1-phenyl-1-propanol hydrochloric acid.

mp 167-169°, alpha$_D$: −27.0° (5% in water) Diastereomeric purity (HPLC): 1-erythro-2-amino-1-phenyl-1-propanol: 86.5%, 1-thero-2-amino-1-phenyl-1-propanol: 13.5%

EXAMPLE 4

Preparation of 1-erythro-2-amino-1-phenyl-1-propanol hydrochloride

With a Ratio of Catalyst Mixture: 1-1-phenyl-1-hydroxy-2-propanone oxime of 0.40:

25 g of sodium hydroxide is dissolved in 350 ml of water. 50 g of 1-1-phenyl-1-hydroxy-2-propanone oxime is added to it. The solution is chilled to −15° C. 20 g of the nickel aluminium catalyst mixture (containing 60 parts by weight of aluminium and 40 parts by weight of nickel) is added to it. The mixture is vigorously stirred at −15° C. and then the temperature is allowed to rise. An exotherm sets in and temperature increases up to 55° C. 200 ml of 1,2-dichloroethane is added to the mixture and the catalyst sludge is filtered. 1,2-Dichloroethane is separated from the filtrate and aqueous layer is extracted again with 100 ml of 1,2-dichloroethane. The combined organic layer is washed with 100 ml water, dried over sodium sulphate and solvent removed in vacuo.

This gives 38 g of 1-erythro-2-amino-1-phenyl-1-propanol base. This is dissolved in absolute ether and treated with ethanolic hydrogen chloride to give 1-erythro-2-amino-1-phenyl-1-propanol hydrochloric acid.

mp 171-172°, alpha$_D$: −31.5° (5% in water) Diastereomeric purity (HPLC): 1-erythro-2-amino-1-phenyl-1-propanol: 96.8%, 1-thero-2-amino-1-phenyl-1-propanol: 3.2%

The effect of different ratios of aluminium: nickel in the catalyst and the ratio of catalyst: oxime on the Diastereomeric purity and yield as seen in the above Examples can be summarized in the following Table I:

It would be clearly apparent from the above Table I that ratios of aluminium: nickel in the catalyst below 1.5 and above 5.0 reduce the diastereomeric purity as well as yield. Similarly it is apparent by comparing results of Example 1B and Example 4 that the ratio of catalyst: oxime at 0.4 affects the diastereomeric purity and yield and any lower ratios will further reduce the purity and yields.

The invention claimed is:

1. A process for preparation of 1-erythro-2-amino-1-phenyl-1-propanol from 1-1-phenyl-1-hydroxy-2-propanone comprising:
   i) reacting 1-1-phenyl-1-hydroxy-2-propanone with an oximation agent in the presence of a base to form 1-1-phenyl-1-hydroxy-2-propanone oxime
   ii) reducing 1-1-phenyl-1-hydroxy-2-propanone oxime using nickel aluminium catalyst mixture as reducing agent
   to obtain crude optically active 1-erythro-2-amino-1-phenyl-1-propanol base.

2. A process as claimed in claim 1 wherein the oximation agent used is a hydroxylamine salt.

3. A process as claimed in claim 2 wherein the hydroxylamine salt is selected from a group comprising of hydrochloride, hydrobromide, sulphate and orthophosphate.

4. A process as claimed in claim 1 wherein the molar ratio of oximation agent to 1-1-phenyl-1-hydroxy-2-propanone is between 0.7 and 2.5, more preferably, between 1.0 and 1.50.

5. A process as claimed in claim 1 wherein the base used for reaction is selected from a group comprising of sodium carbonate, sodium hydrogen carbonate, sodium hydroxide, sodium acetate, potassium carbonate, potassium hydroxide, potassium acetate, calcium hydroxide, barium hydroxide, preferably, sodium hydroxide or sodium hydrogen carbonate.

6. A process as claimed in claim 1 wherein the temperature used for the reaction in step i) is between −5° C. and 70° C., preferably between 0° C. and 30°.

7. A process as claimed in claim 1 wherein the pH of reaction mass is maintained between 6.0 and 10.0, preferably between 7.0 and 8.0.

8. A process as claimed in claim 1 wherein the reducing agent used is a catalyst mixture comprising of aluminium and nickel metals in a ratio of 1.5 to 5.0 by weight.

9. A process as claimed in claim 1 wherein the catalyst mixture used is at least 0.4 to 1.0 times more preferably at least 0.6 to 1.0 times by weight of the 1-1-phenyl-1-hydroxy-2-propanone oxime.

10. A process as claimed in claim 1 wherein the crude optically active 1-erythro-2-amino-1-phenyl-1-propanol is treated to get a pure isomer of 1-erythro-2-amino-1-phenyl-1-propanol.

TABLE I

Comparative data for Diastereomeric purity and yield obtained in the Examples 1, 3 and 4:

| Example No | Aluminium: Nickel metals ratio in catalyst | Catalyst: Oxime ratio | Diastereomeric purity | | % Yield |
| | | | 1-erythro-2-amino-1-phenyl-1-propanol | 1-thero-2-amino-1-phenyl-1-propanol | |
|---|---|---|---|---|---|
| Example 1B | 1.5 | 0.6 | 97.5% | 2.5% | 98% |
| Example 3A | 1.22 | 0.6 | 83.8% | 16.2% | 63.37% |
| Example 3B | 5.67 | 0.6 | 86.5% | 13.5% | 49.17% |
| Example 4 | 1.5 | 0.4 | 96.8% | 3.2% | 83.05% |

11. A process as claimed in claim 1 wherein the crude 1-erythro-2-amino-1-phenyl-1-propanol is treated preferably with an organic acid in presence of a solvent and the salt so formed is decomposed using a base.

12. A process as claimed in claim 11 wherein the organic acid is preferably selected from a group comprising of acetic acid, propionic acid, butyric acid, isobutyric acid, oxalic acid, malonic acid, succinic acid, cyclohexane carboxylic acid, benzoic acid, p-toluic acid, methanesulphonic acid or p-toluenesulphonic acid.

13. A process as claimed in claim 11 wherein the solvent used for the process is either water or a lower aliphatic alcohol selected form a group comprising of methanol, ethanol, isopropyl alcohol, n-butanol, 2-butanol and tert-butanol or a mixture of water and one of these alcohols or a mixture of two of these alcohols.

14. A process as claimed in claim 11 wherein the temperature of reaction of crude 1-erythro-2-amino-1-phenyl-1-propanol with the organic acid is between 0° and the boiling point of the solvent at atmospheric pressure.

15. A process as claimed in claim 11 wherein the base used for decomposition of the salt of pure 1-erythro-2-amino-1-phenyl-1-propanol with organic acid is selected from a group comprising of sodium carbonate, sodium hydrogen carbonate, sodium hydroxide, sodium acetate, potassium carbonate, potassium hydroxide, potassium acetate, calcium hydroxide, barium hydroxide, preferably, sodium hydroxide or sodium hydrogen carbonate.

* * * * *